United States Patent [19]

Hunnicutt

[11] Patent Number: 5,269,320

[45] Date of Patent: Dec. 14, 1993

[54] PROPHYLACTIC-CONTRACEPTIVE BARRIERS WITH SHIELD FLANGE AND ATTACHED UNDERGARMENT

[76] Inventor: Jane Hunnicutt, P.O. Box 833, Sebastopol, Calif. 95472-0833

[21] Appl. No.: 57,291

[22] Filed: Jun. 2, 1987

[51] Int. Cl.⁵ .............. A61F 6/06; A61F 6/02; A61F 5/44
[52] U.S. Cl. .................. 128/830; 128/842; 604/347; 604/349; 604/352; 604/353
[58] Field of Search .................. 604/347–353, 604/347–353; 2/408; 128/132 R, 767, 830, 842

[56] References Cited

U.S. PATENT DOCUMENTS

| | | | |
|---|---|---|---|
| D. 288,485 | 2/1987 | Denno | D2/10 X |
| 2,396,599 | 3/1946 | O'Brien | 2/408 |
| 2,873,740 | 2/1959 | Wainwright | 604/349 |
| 3,536,066 | 10/1970 | Ludwig | 128/132 R |
| 4,233,978 | 11/1980 | Hickey | 604/347 |
| 4,284,079 | 8/1981 | Adair | 128/767 |
| 4,638,790 | 1/1987 | Conway et al. | 604/352 X |
| 4,664,104 | 5/1987 | Jaicks | 604/353 X |
| 4,713,066 | 12/1987 | Komis | 604/349 X |
| 4,807,611 | 2/1989 | Johnson | 604/349 X |
| 4,834,113 | 5/1989 | Reddy | 128/830 |
| 4,834,114 | 5/1989 | Boarman | 604/347 X |
| 4,840,624 | 6/1989 | Lee | 604/349 |

FOREIGN PATENT DOCUMENTS 48606 6/1986 Japan ................ 604/349

Primary Examiner—Randall L. Green
Assistant Examiner—Elizabeth M. Burke

[57] ABSTRACT

Barriers for preventing contraception and disease transmission comprise, in the simplest embodiment, a tubular or cylindrical shield (12, 38) of rubber to isolate the penis from the vagina and an attached flange portion (14) to shield the area surrounding the penis and vagina. The underside of the flange has adhesive (16) around the edge border to retain the flange in place. The device may be used by a female partner and is more effective than a condom since it shields the surrounding area. The device may be formed as part of a panty (30) or man's brief (70) so that the female can control prophylaxis and contraception, or the subordinate male in gay sex can control prophylaxis. The tubular rubber shield is provided in a compacted, folded state (38) with a lubricant (54, 56) and a lubricant-impervious covering (20, 22, 58, 66). When made part of an undergarment, the inner side of the shield is covered with a layer of cotton (62) for comfort. The crotch portion (34) of the undergarment may be made detachable so that the upper part of the undergarment can be reused.

18 Claims, 3 Drawing Sheets

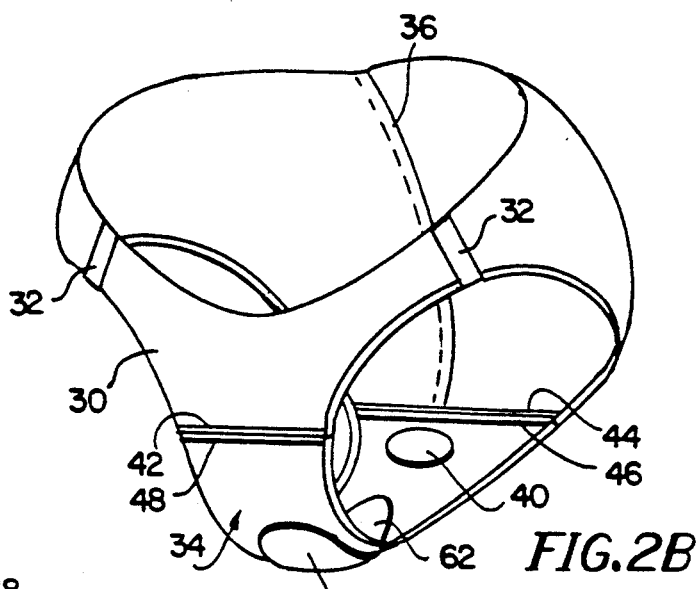
FIG.2B
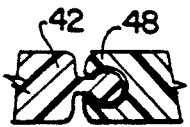
FIG.2F
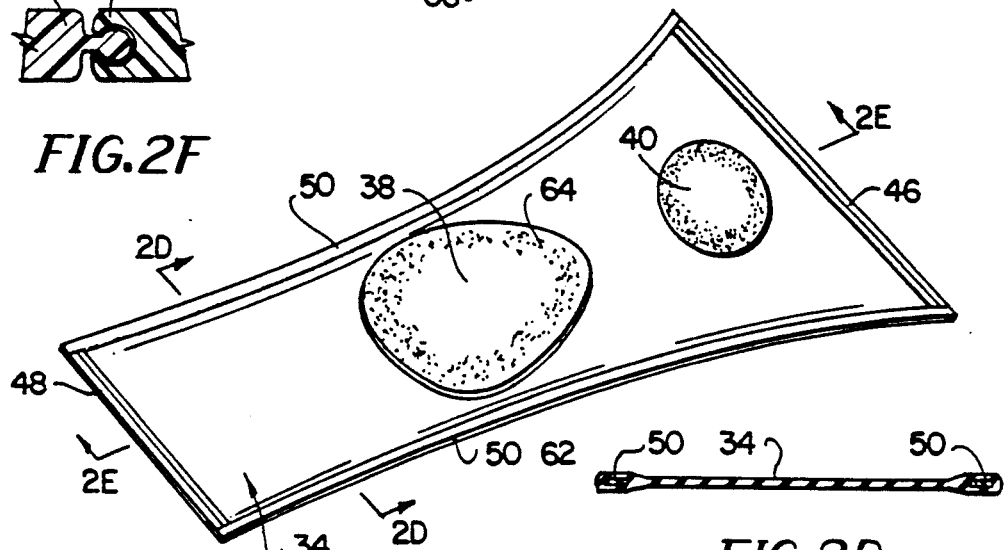
FIG.2C
FIG.2D
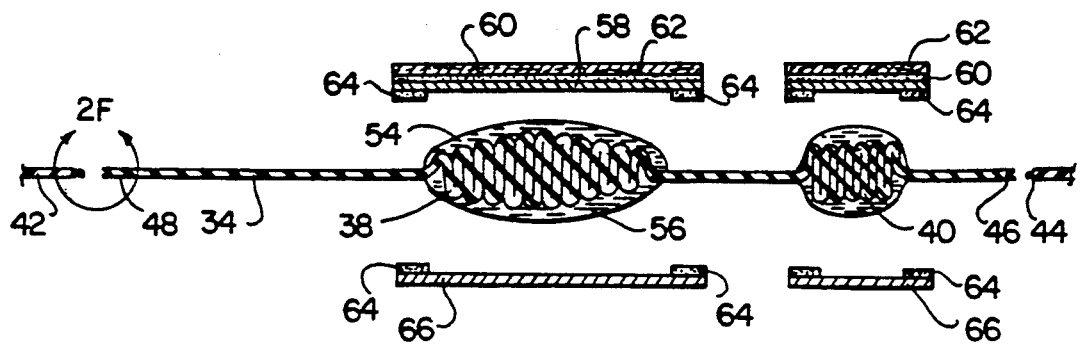
FIG.2E

PROPHYLACTIC-CONTRACEPTIVE BARRIERS WITH SHIELD FLANGE AND ATTACHED UNDERGARMENT

BACKGROUND

1. Field Of Invention

This invention relates to sexual barriers for preventing transmission of disease-producing microorganisms and fertilizing spermatazoa. Specifically it relates to such barriers which have increased ease of use and enhanced shielding ability.

2. Description Of Prior Art

The familiar condom or sexual barrier which was placed over the man's penis has been used since ancient times to prevent conception and, more recently, to prevent transmission of disease-producing microorganisms (viruses and bacteria). While highly effective if it remains intact and in place during coitus, it suffers from a number of serious disadvantages which have prevented its widespread use and implementation.

First are the problems of spontaneity and interruption of sexual activity. The condom must usually be unrolled and placed over the man's penis after he achieves erection. Since this requires time and departure by both partners from more pleasurable activity of pre-coital mutual stimulation, it detracts from and interrupts the overall spontaneity and pleasure of the act, deterring sexual partners, from, and creating a generally negative attitude toward, its use.

Second is the problem of control by the male partner. Heretofore condoms either had to be positioned by the male partner on his erect penis, or by the female partner provided the male first gave permission (expressly or tacitly). Thus the use of the condom was under the direct or permissive control of the male. If the male did not want to use the condom, he had the power to refuse to place it on himself, or to refuse to allow the female to place it on him.

Third is the problem of efficacy in disease prevention, hereinafter prophylaxis. The usual condom covers only the penis, but medical experts have noted that disease often is transmitted between the sexual partners' public hairs and around the condom due to occasional intermingling of the partners' sexual lubricants and other fluids.

The above problems are also present if anal sex is practiced, either by heterosexuals or homosexual male partners.

Ludwig, in U.S. Pat. No. 3,536,066, 1970, shows an appliance to be worn by a woman over her legs and which contains a bellows-like probiscus in the center. This appliance is highly awkward for the woman to use, is very uncomfortable for both the woman and the man while in use, and its placement would interfere with spontaneity and interrupt sexual activity. Because of its awkward shape, it is doubtful that Ludwig's device would stay in place or would allow natural feeling to occur.

Freimark, in U.S. Pat. No. 4,004,591, 1977, shows a condom with extending side flaps at its base to facilitate withdrawal and maintain position during use. However this device provides little more shielding than the usual condom and suffers from all of its other disadvantages, aforenoted. In addition, it has an apparently uncomfortable central protrusion which would prevent adequate clitoral contact and the device lacks means to hold itself in place. Conway, Conway, and Conway, in U.S. Pat. No. 4,638,790, 1987, show a complex condom with adhesive coatings. This device, however, still suffers from all of the above disadvantages of condoms in general, and in particular, has a high cost due to its complexity.

OBJECTS AND ADVANTAGES

Accordingly, several objects and advantages of the invention are to provide a prophylactic-contraceptive (here abbreviated "pro-con") device which can be used without interruption of sexual activity, without detraction from sexual spontaneity, which can be implemented under the full control of the female, which does not require the male's permission or action for placement, and which is highly effective in preventing disease transmission via pubic hair contact or intermingling of sexual fluids. Further objects and advantages will be come apparent from a consideration of the ensuing description and drawings.

DRAWING FIGURES

FIG. 2b is a perspective detailed view of the panty of FIG. 2a.

FIG. 2c is a perspective view of the crotch section of the panty of FIG. 2b.

Figure 2H:
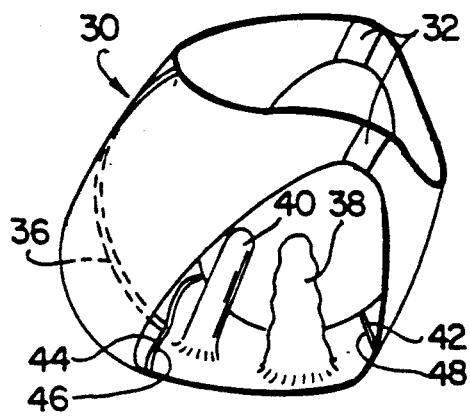
Figure 2G:
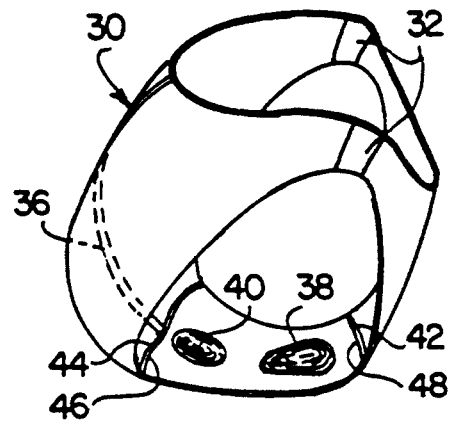
Figure 2A:
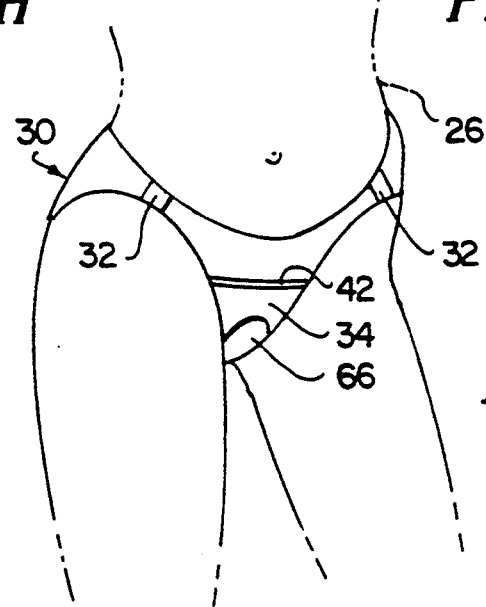
FIG. 2a is a perspective view of a woman's pro-con panty as worn on a woman.

FIGS. 2d and 2e are cross-sectional (XS) and XS exploded views taken in the directions indicated by the lines 2d—2d and 2e—2e of FIG. 2a.

FIG. 2f is an enlarged view of area 2f of FIG. 2e.

FIG. 2g is a perspective view of the panty as if worn with protective coverings removed.

FIG. 2h is a perspective view of the panty as if in use during coitus.

Figure 3B:
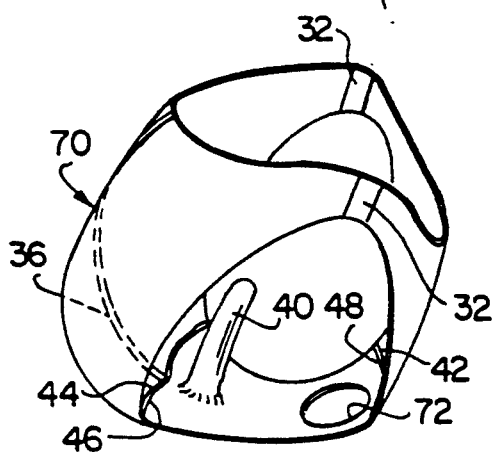
Figure 3A:
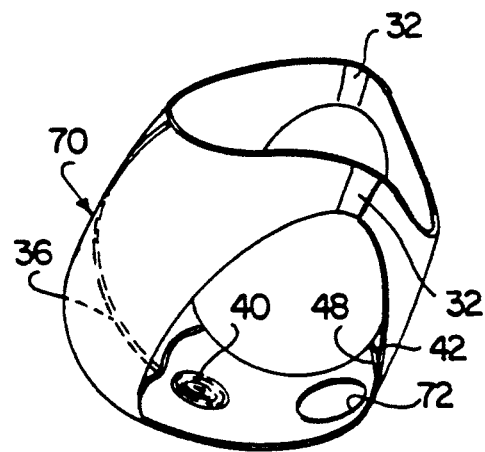

FIG. 3a is a perspective view of a gay man's prophylactic brief prior to use.

FIG. 3b is a perspective view of same as if in use.

DRAWING REFERENCE NUMERALS 10 pro-con shield
12 cylindrical portion of 10
14 flange portion of 10
16 inner adhesive layer
18 lubricant
20 bottom release paper
22 top release paper
24 adhesive on 22
26 female
28 pudendum
30 panty
32 fasteners
34 crotch section
36 seam
38 vaginal shield
40 anal shield
42 male front fastener
44 male rear fastener
46 female rear fastener
48 female front fastener
50 elastic strip
52 flat part
54 female lubricant 56 male lubricant
58 inner paper seal
60 fabric-to-paper adhesive
62 cotton inner layer
64 paper-to-latex adhesive
66 paper outer seal
77 gay brief
72 penis opening

DESCRIPTION

Figure 1A:
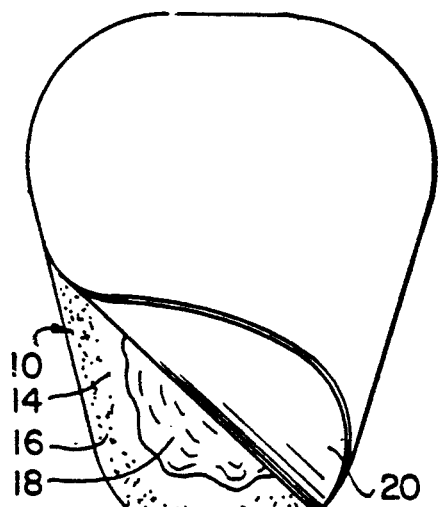
FIG. 1a is a plan view of a pro-con shield according to the invention.
Figure 1B:
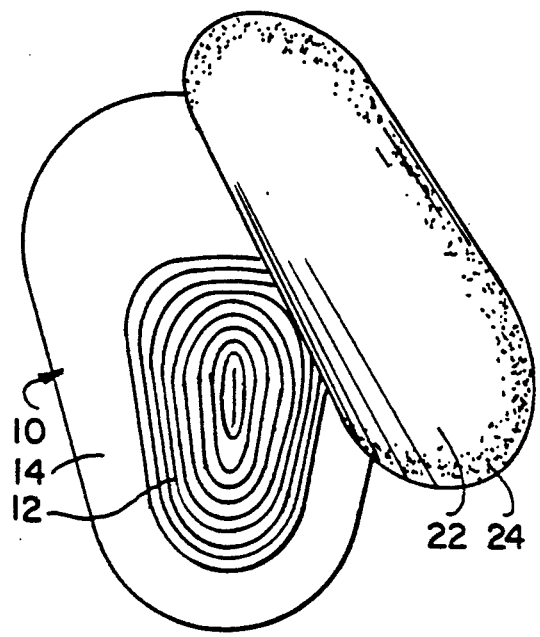
FIG. 1b is a bottom view of same.
Figure 1C:
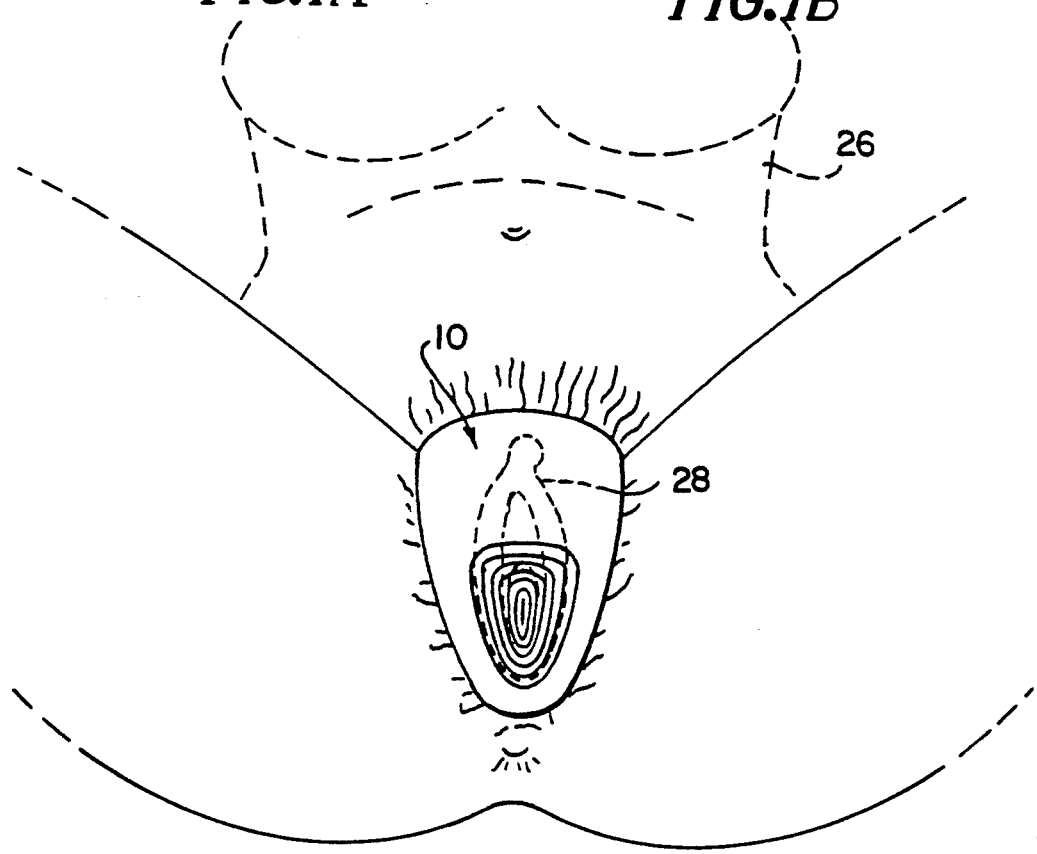
FIG. 1c is a perspective view of same in position on a woman.

FIGS. 1a To 1c—Pro-Con Shield

FIGS. 1a to 1c show a prophylactic-contraceptive (pro-con) shield according the invention. As shown in FIGS. 1a and 1b, the shield comprises a rubber membrane 10 having an elongated, vaginal-lining cylindrical portion 12 (shown compacted and folded prior to use) and a flange or outer shield portion 14. Portion 12 is long enough to cover an erect penis and has a closed end to contain seminal fluid and provide a complete barrier, similar to that of a conventional condom. However, as stated and shown, instead of being rolled, portion 12 is compressed into a folded, flat mass as indicated so as to be in a compact shape which is generally coplanar with the flange portion.

FIG. 1a shows the bottom or female-facing side of the shield. The edge of flange portion 14 is covered by a layer of pressure-sensitive adhesive 16. The inside of elongated portion 12 is covered by a blob of lubricant 12. The entire bottom side of the shield, including flange portion 14, its adhesive coating 16, and lubricant 18, is covered by a non-absorbent release paper 20, which is shown partially peeled off.

FIG. 1b shows the top or male-facing side of the shield. The entire bottom side of the shield, including flange portion 14 and elongated portion 12, is covered by a non-absorbent release paper 22. Since the outer side of flange portion 14 has no adhesive, the edge of release paper 22 contains a layer of adhesive 24 to enable paper 22 to remain in place on shield 10. Optionally, the outside of elongated portion 12 may also be covered by a blob of lubricant (not shown) similar to blob 18 on the underside. The outside or male lubricant may include a spermicide. As indicated below, the shield of FIGS. 1a to 1c is incorporated as part of the pro-con panty of FIGS. 2a to 2e. A cross-sectional view of the shield of FIGS. 1a to 1c would appear as in the center portion of FIG. 2e, with folded portion 38 corresponding to portion 12, paper layer 58 corresponding to release paper 20, and paper layer 66 corresponding to release paper 22.

As indicated in FIGS. 1a and 1b, flange portion 14 has a generally triangular shape with curved corners. Two of the sides of the triangle are equal and longer than the third or base side. Its actual dimensions are approximately to the scale shown, with a height of about 11 cm, and a width, at its maximum dimension near its top of about 7 cm. Flange area 14 is about 3 cm wide in the bottom and sides and is about 5 cm wide at the top in order to cover the clitoral-urethreal area of the female. The edge of portion 14 is shown as plain, but it may have a slightly increased thickness or a rolled edge (not shown). The device is preferably sold in a hermetically-sealed foil or plastic package.

OPERATION

FIGS. 1—Pro-Con Shield

As shown in FIG. 1c, the shield of FIGS. 1a and 1b is installed by a female partner 26 prior to coitis by removing bottom release paper 20, spreading her legs as shown, and placing the shield over her pudendum 28. The base side of the triangle is positioned upwardly so that the relatively wide area of flange portion 14 covers her urethreal-clitoral area. Adhesive layer 16 will remain on portion 14 so that it will hold the shield to the female in the position shown with adequate tenacity. Even if she then closes her legs, shield 10 will remain in position due to the adhesive effect of layer 16 and the high flexibility of flange portion 14.

Either partner then will remove top release paper 22. The male partner then inserts his penis. As the erect penis is inserted, it will push and extend compacted and folded cylindrical portion 12 of the shield into the vagina. Upon full insertion, the shield will not only cover the penis, but also the surrounding areas, around the vagina and the base of the penis, thereby providing a far more effective shield. Due to adhesive layer 16, the shield will remain in place during the usual reciprocating motions of coitus and even after withdrawal. The female thus continues to retain control and can remove the shield at her pleasure.

The reader will see that the shield provides a superior barrier to sperm and microorganisms without affecting spontaneity and interruption of sexual activity. This is because it can be installed well prior to coitus, thus not requiring time and departure by both partners from more pleasurable activity of pre-coital mutual stimulation. Also since the shield is under control of the female partner, she is no longer dependent upon the male for contraception or prophylaxis. The shield is more effective in disease prevention since it shields not only the penis, but the sexual partners' pubic hair areas as well due to its flange portion.

DESCRIPTION

FIGS. 2a To 2e—Pro-Con Panties

In accordance with another aspect of the invention, I provide a pro-con panty 30 which incorporates the principles and the shield of FIGS. 1a to 1c. As shown in FIG. 2a, panty 30 in overall appearance resembles a conventional panty. It is shown with waist or side fasteners 32 (which may be snap or hook fasteners) for ease of removal, but these can be eliminated in favor of a pull-on-type panty with an elastic waistband (not shown). It has a removable and replaceable crotch section 34 which provides contraceptive and prophylactic action according to the invention.

As shown in FIG. 2b, panty 30 has an elastic back seam 36 which inhibits slippage of the panty and which aids in shaping the wearer's anatomy. Crotch section 34 has a front, vaginal shield or pro-con part 38 (FIGS. 2c and 2g) and an optional rear, anal shield part 40. The upper part of panty 30 preferably is made of cotton, nylon, or the like, as in a conventional panty, whereas crotch section 34 is made generally of rubber, as will be described.

FIG. 2c shows crotch section 34 per se. It is generally rectangular in shape, elongated, and made of rubber. Its ends have elongated fasteners 48 and 46 (see enlarged view of FIG. 2f) for attachment to the rest of the panty, with rear fastener 46 being slightly longer. Its sides have imbedded elastic bands or strips 50 (shown in the cross-sectional view of FIG. 2d) and flare gradually from the front end (adjacent fastener 48) to the rear end (adjacent fastener 46).

As shown in FIG. 2f, fastener 48 is a female fastener which mates with a male fastener 42 on the upper part of the panty. Fastener 42 comprises, in cross-section, a ball-on-pedestal-type male member of firm plastic. Fastener 48 has an elongated mating female recess of resilient plastic. At the rear of crotch section 34, a similar elongated female fastener 46 (FIGS. 2c and 2e) is provided to mate with a similar elongated male fastener 44 (FIG. 2e) on the upper part of the panty. Alternatively other fasteners can be used, such as a multiple-interfitting-rib-type fastener used on transparent plastic lunch bags and sold under the trademark ZIP-LOCK by The Dow Chemical Corp. of Indianapolis, Ind. 46268, a multiple-hook-and-loop fastener sold under the trademarks VELCRO and LATCHLOCK, or multiple snap fasteners. Also the crotch section can be permanently joined to the upper part of the panty, in which case the entire panty would be disposable. In the latter case, the upper part of the panty may be made of paper to minimize cost.

As shown in FIG. 2e, an exploded (cross-sectional) view taken at 2e—2e of FIG. 2c, vaginal and anal shield parts 38 and 40 are identical, except that vaginal shield part 38 is larger. Thus only vaginal shield part 38 will be detailed.

Part 38 comprises, at its center, a compressed, folded cylindrical vaginallining part 38, similar to cylindrical part 12 of FIG. 1a. Shield part 38 is integral with the rest or flat part 52 of crotch section 34. Both sides of shield part 38 are covered with respective layers of lubricant 54 (inner, for the female) and 56 (outer, for the male).

The inner, female side (upper side of FIG. 2e) is then covered by a paper layer 58, a layer of adhesive 60, and a final layer of cotton 62. Cotton layer 62 is visible in FIGS. 2b and 2c. Paper layer 58 is adhered to the inner (upper) side of flat part 52 by a border adhesive layer 64 which is weaker than layer 60.

The outer, male side (lower side of FIG. 2e) is covered by a paper layer 66 which is adhered to the outer (lower) side of flat part 52 by a border adhesive layer 68. Paper layer 66 is partially visible in FIG. 2b.

The purpose of paper layers 58 and 66 is to shield and prevent access to lubricant layers 54 and 56 when the panty is worn. Adhesive layer 60 keeps cotton and paper layers 58 and 62 together permanently, while weaker adhesive border layers 64 and 68 keep paper 66, and the laminar assembly of paper 58, adhesive 60 and cotton 62, on flat part 52 until ready for use. Cotton layer 62 provides a comfortable, soft part adjacent the sensitive pudendum of the wearer. In lieu of cotton and paper layers 62 and 58, a single cotton layer (not shown) may be used, provided its lower side (FIG. 2e) is covered with a lubricant barrier. Also the cotton layers of both shields 38 and 40 may be interconnected and may extend over the entire crotch portion.

OPERATION

FIGS. 2g and 2h—Pro-Con Panty

In operation, the woman wears the panty as shown in FIG. 2a whenever she expects that she may have intercourse, but desires prophylaxis and/or contraception. If intercourse is about to occur, she will leave panty 30 in place, but will reach under crotch portion 34 and remove cotton layer 62 and adhered paper layer 58. This will expose compacted, folded cylindrical shield 38, as indicated in FIG. 2g. Either the man or the woman can remove outer paper layer 66. Lubricant layers 54 and 56 and compacted, folded rubber cylindrical portion 50 will now be exposed. The man can then insert his penis. As before in connection with FIGS. 1a to 1c, such insertion will push out portion 38 into the vagina and cause it to surround the penis, thereby providing an effective shield, as indicated at 38 in FIG. 2h. The external pudenda will also be well shielded by flat part 52 of the crotch portion.

If the partners desire to have anal intercourse, the same process is performed with rear shield 40, whereupon an anal shield will be accessible as indicated at 40 in FIGS. 2g and 2h.

After climax, the man will withdraw his penis, leaving the panty in position and the cylindrical part in or withdrawn from the vagina (or anus). The woman can now remove the panty, wash herself, and put on a new panty. The used pro-con panty can be reused by replacing crotch section 34. This is done by peeling fasteners 42 and 44 out of their retainers on the top portion of the panty, discarding the crotch portion, washing the cloth top partition, and attaching a new crotch portion by inserting male fasteners 42 and 44 (on the upper part of the panty) into female fasteners 48 and 46, respectively (on crotch portion 34). This will provide a renewed panty as shown in FIG. 2b. Alternatively, if the crotch portion is permanently attached to the upper part, the entire panty can be discarded.

As with the previous embodiment, the reader will see that the panty provides a superior barrier to sperm and microorganisms without affecting spontaneity and interruption of sexual activity. This is because it is put on well prior to coitus, thus not requiring time and departure by both partners from more pleasurable activity of pre-coital mutual stimulation. Also since the panty is under control of the female partner, she is no longer dependent upon the male for contraception or prophylaxis. The shield is more effective in disease prevention since it shields not only the penis, but the sexual partners' pubic hair areas as well due to its flange portion.

FIG. 3a And 3b—Gay Man's Briefs

The principles of the above panty can be applied to prophylaxis briefs for a gay man. As shown in FIG. 3a, a gay man's briefs (shorts or underpants) 70 include a front opening 72 where the penis is located and a rear shield portion 40 which is identical to shield portion 40 of FIG. 2e. In FIG. 3a, shield portion 40 is shown with the inner paper and cotton layers removed, thereby exposing the lubricant and the cylindrical shield. Opening 72 may optionally be covered by a removable cotton cover (not shown) which can be attached over the opening by snaps or the like.

When a gay couple desire to have anal intercourse, the dominant partner will extend his penis through opening 72, or he can even remove the briefs entirely. The other, subordinate and quasi-female partner will leave his briefs on, removing the inner cotton layer and its attached paper layer, together with the outer paper layer over shield 40, thereby exposing the rubber cylindrical shield as shown in FIG. 3a. The dominant partner will insert his penis, causing the cylindrical rubber shield to extend, as shown in FIG. 3b.

Thus the reader will see that the brief of the invention will enable gay men to have anal intercourse which prophylaxis without removing their briefs and without requiring either partner to install a condom. In addition, the briefs provide far superior prophylacic shielding than a condom and do not require any more than a trivial interruption of sexual activity.

SUMMARY, RAMIFICATIONS, AND SCOPE

Accordingly it is seen that, according to the invention, I have provided contraceptive and prophylactic devices and garments which solve all of the aforementioned problems of prior-art contraceptive means and which are simple, economical, and reliable.

While the above description contains many specificities, these should not be construed as limitations on the scope of the invention, but as exemplifications of the presently-preferred embodiments thereof. Many other ramifications and variations are possible within the teachings of the invention. For example, the flange of FIGS. 1a to 1c can have a different shape, the panty and belief can have different shapes, opening 72 in the briefs of FIGS. 3a and 3b can be omitted, the entire brief can be made of rubber with suitable cotton lining, etc.

Thus the scope of the invention should be determined by the appended claims and their legal equivalents, and not by the examples given.

I claim:

1. A prophylactic or contraceptive device adapted to be worn by a female, comprising:
    a flexible, liquid-impervious membrane comprising a sheath portion and a flange portion,
    said sheath portion being in a folded state comprising a plurality of tightly compacted folds disposed substantially in a plane and being unfoldable and extendable to form a cylinder having an axis extending an a direction generally perpendicular to the plane of the sheath portion in its folded state, said cylinder having an open end proximal to the flange portion and a closed end distal to said flange portion,
    said flange portion being integral with the sheath portion and extending in a direction generally coplanar with the plane of the sheath in the folded state,
    a coating of lubricant on both sides of the sheath portion, and
    adhesive means on one side of the flange portion for affixing the device to the pudendum of a female wearing the device so that the flange portion covers and shields the pudendum.

2. The device of claim 1 wherein said flange portion has a generally triangular shape.

3. The device of claim 1 wherein one side of said sheath portion is coated with a layer of a lubricant.

4. The device of claim 3 wherein the side of said sheath portion which is coated with a layer of a lubricant is additionally covered with a protective membrane layer.

5. The device of claim 1 wherein said sheath and flange portions are covered on both sides with a protective membrane layer.

6. A prophylactic or contraceptive device adapted to be worn by a female, comprising:
    a flexible, liquid-impervious membrane comprising a sheath portion and a flange portion,
    said sheath portion being in a folded state comprising a plurality of tightly compacted folds disposed substantially in a plane and being unfoldable and extendable to form a cylinder having an axis extending in a direction generally perpendicular to the plane of the sheath portion in its folded state, said cylinder having an open end proximal to the flange portion and a closed end distal to said flange portion,
    said flange portion being integral with the sheath portion and extending in a direction generally coplanar with the plane of the sheath in the folded state,
    an adhesive on one side of the flange portion for affixing the device to the pudendum of a female wearing the device so that the flange portion covers and shields the pudendum,
    a layer of lubricant on both sides of the sheath portion, and
    membrane layers covering both sides of the flange and sheath portion so as to shield the adhesive and the lubricant 7. The device of claim 6 wherein said flange portion has a generally triangular shape.

8. The device of claim 6 wherein said sheath and flange portions are made of rubber.

9. The device of claim 6 wherein said sheath and flange portions are made of rubber and at least one of said protective membrane layers is made of paper.

10. The device of claim 6, further including a brief garment having a buttocks-covering section a crotch-covering section, and a waistband, with the flange portion of the device being attached to and forming a part of the crotch-covering section of the garment.

11. A prophylactic or contraceptive garment adapted to be worn by a person, comprising:
    an undergarment having a waistband, a buttocks-covering section and a crotch section, and
    a prophylactic and/or contraceptive shielding device forming an integral part of the crotch section, said device comprising:
    a flexible, liquid-impervious membrane comprising a sheath portion and a flange portion,
    said sheath portion being in a folded state comprising a plurality of tightly compacted folds disposed substantially in a plane and being unfoldable and extendable to form a cylinder having an axis extending in a direction generally perpendicular to the plane of the sheath portion in its folded state, said cylinder having an open end proximal to the flange portion and a closed end distal to said flange portion,
    said flange portion being integral with the sheath portion and extending in a direction generally coplanar with the plane of the sheath in the folded state.

12. The garment of claim 11, further including means for removably attaching the crotch section of the garment to the waistband and the buttocks-covering section whereby the crotch section can be detached and replaced after use.

13. The garment of claim 12 wherein said crotch section of said garment is made generally of a liquid-impermeable material and is integral with said shield device.

14. The garment of claim 11 wherein the crotch section of the garment contains a plurality of said shielding devices, one positioned to cover the vagina of a female wearing the garment and another positioned to cover the anus of said female.

15. The garment of claim 11 wherein at least one side of said shield device is coated with a lubricant and an overlying protective layer which is liquid impervious.

16. A prophylactic or contraceptive garment adapted to be worn by a person, comprising:

an undergarment having a waistband, a buttocks-covering section and a crotch section, and a prophylactic and/or contraceptive shielding device forming an integral part of the crotch section, said device comprising:

a flexible, liquid-impervious membrane comprising a sheath portion and a flange portion, said sheath portion being in a folded state comprising a plurality of tightly compacted folds disposed substantially in a plane and being unfoldable and extendable to form a cylinder having an axis extending in a direction generally perpendicular to the plane of the sheath portion in its folded state, said cylinder having an open end proximal to the flange portion and a closed end distal to said flange portion, said flange portion being integral with the sheath portion and extending in a direction generally coplanar with the plane of the sheath in the folded state, a liquid impervious protective layer which covers both sides of the sheath portion of the shielding device in the folded state, and a coating of lubricant on inner and outer sides of the sheath portion of said device.

17. The garment of claim 16 wherein the protective layer on one side of the crotch section is made of cloth.

18. A prophylactic or contraceptive garment adapted to be worn by a person, comprising:

an undergarment having a waistband, a buttocks-covering section and a crotch section, and a prophylactic and/or contraceptive shielding device forming an integral part of the crotch section, said device comprising:

a flexible, liquid-impervious membrane comprising a sheath portion and a flange portion, said sheath portion being in a folded state comprising a plurality of tightly compacted folds disposed substantially in a plane and being unfoldable and extendable to form a cylinder having an axis extending in a direction generally perpendicular to the plane of the sheath portion in its folded state, said cylinder having an open end proximal to the flange portion and a closed end distal to said flange portion, said flange portion being integral with the sheath portion and extending in a direction generally coplanar with the plane of the sheath in the folded state, and an opening in the crotch section of the garment separate from said shield device.

* * * * *